United States Patent [19]

Genet et al.

[11] Patent Number: 5,426,216
[45] Date of Patent: Jun. 20, 1995

[54] PROCESS FOR THE HYDROGENATION OF ETHYLENICALLY UNSATURATED ORGANIC COMPOUNDS AND RUTHENIUM CATALYSTS FOR CARRYING OUT SAID PROCESS

[75] Inventors: Jean-Pierre Genet, Verrières-le-Buisson; Sylvain Juge, Orsay; Jean A. Laffitte, Pau; Catherine Pinel, Ablis; Sergio Mallart, Orsay, all of France

[73] Assignee: Society Nationale Elf Aquitaine, Courbevoie, France

[21] Appl. No.: 81,314

[22] PCT Filed: Dec. 27, 1991

[86] PCT No.: PCT/FR91/01077
§ 371 Date: Aug. 12, 1993
§ 102(e) Date: Aug. 12, 1993

[87] PCT Pub. No.: WO92/12110
PCT Pub. Date: Jul. 23, 1992

[30] Foreign Application Priority Data

Dec. 28, 1990 [FR] France .................... 90 16414

[51] Int. Cl.⁶ ............ C07C 229/00; C07F 9/00; B01J 31/00
[52] U.S. Cl. .................. 562/450; 556/21; 556/136; 502/162
[58] Field of Search ......... 556/21, 136; 502/162; 562/450

[56] References Cited

U.S. PATENT DOCUMENTS

| 5,004,823 | 4/1991 | Devon et al. | 556/136 |
| 5,177,231 | 1/1993 | Manimaran et al. | 556/136 |
| 5,190,905 | 3/1993 | Kolich et al. | 556/21 |
| 5,198,562 | 3/1993 | Noyuri et al. | 556/21 |
| 5,200,539 | 4/1993 | Stanley et al. | 556/21 |
| 5,223,648 | 6/1993 | Hermann et al. | 556/21 |

FOREIGN PATENT DOCUMENTS

| 0271311 | 6/1988 | European Pat. Off. | 556/21 |
| 0272787 | 6/1988 | European Pat. Off. | |
| 0366390 | 5/1990 | European Pat. Off. | |

OTHER PUBLICATIONS

Journal of Organic Chemistry, vol. 52, No. 14, 10 Jul. 1987, Easton U.S. pp. 3174–3176; T. Ohta, et al. "Asymmetric Hydrogenation of Unsaturated Carboxylic Acids Catalyzed by Binap–Ruthenium (II) Complexes".

Journal of the Chemical Society, Section A 1971, London, pp. 16–20; M. Cooke, et al. "Pi-Allylic Complexes of Ruthemium".

Primary Examiner—Raymond Henley, III
Assistant Examiner—Keith MacMillan
Attorney, Agent, or Firm—Ostrolenk, Faber, Gerb & Soffen

[57] ABSTRACT

The present invention relates to a process for the hydrogenation of ethylenically unsaturated organic compounds. This process is carried out in a homogeneous medium containing a hydrogenation catalyst formed by a complex of ruthenium with a phosphine, which comprises two allylic groups as ligands on the Ru.

17 Claims, No Drawings

PROCESS FOR THE HYDROGENATION OF ETHYLENICALLY UNSATURATED ORGANIC COMPOUNDS AND RUTHENIUM CATALYSTS FOR CARRYING OUT SAID PROCESS

This is a national-phase application filed under 35 USC 371 of PCT application FR 91/01077, filed Dec. 27, 1991.

FIELD OF THE INVENTION

The invention relates to the hydrogenation of ethylenically unsaturated organic compounds having at least one aliphatic C=C double bond. It comprises a process which makes it possible advantageously to carry out such an operation in a homogeneous medium, in the presence of a catalyst formed by a ruthenium complex. It further relates to a catalyst system of Ru with a phosphorus ligand which is capable of effecting asymmetric hydrogenation with an excellent yield and an enantiomeric excess.

PRIOR ART

Neutral ruthenium complexes of the structure bis(2-methylallyl)bis(phosphite)ruthenium are known to have been described in the article by M. COOKE et al., J. Chem. Soc. (A), pages 16–20 (1971). More precisely, these are complexes of the formula

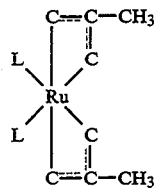

where
- compound (C1): L=(MeO)$_3$P
- compound (C2): L=(EtO)$_3$P
- compound (C3): L=MeC(CH$_2$O)$_3$P
- compound (C4): L=EtC(CH$_2$O)$_3$P
- compound (C5): L=Me$_2$PCH$_2$CH$_2$PMe$_2$ It so happens that said article by M. COOKE et al. neither describes nor suggests the use of these five compounds in the field of the catalytic hydrogenation of ethylenically unsaturated compounds.

Furthermore, it is known that ionic ruthenium complexes have been recommended in the past for the catalytic hydrogenation of olefins. In this connection, see on the one hand EP-A-0 366 390, which recommends for this purpose the use of complexes of the formula $$[RuX_l(L)_m(R\text{-BINAP})]Y_n \qquad (C6)$$

in which
- BINAP is a 2,2'-bis(diphenylphosphino)-1,1'-binaphthyl radical and R is H or CH$_3$ in the 4-position of each phenyl ring of the bis(diphenylphosphino) fragment,
- X is F, Cl, Br or I,
- L is especially benzene, p-cymene or acetonitrile,
- Y is a halogen atom, ClO$_4$, PF$_6$, BF$_4$ or BPh$_4$, and
- when L is other than acetonitrile, l=1, m=1 and n=1, and
- when L is acetonitrile, if l=1 then m=2 and n=1, and if l=0 then m=4 and n=2, and on the other hand EP-A-0 272 787, which recommends the use of the complexes of the formula $$Ru_xH_yCl_z(R^4\text{—BINAP})_2(S)_p \qquad (C7)$$

in which
- BINAP is as defined above in formula C6,
- R$^4$ is defined in the same way as R above in formula C6,
- S is a tertiary amine, and
- when y=0 then x=2, z=4 and p=1, and
- when y=1 then x=1, z=1 and p=0.

Furthermore, the article by T. OHTA et al., J. Org. Chem., 52, pages 3174–3176 (1987), has disclosed neutral ruthenium catalysts for the hydrogenation of carboxylic acids ethylenically unsaturated in the alpha,beta or beta,gamma-positions. These catalysts, which have the S or R configuration, are represented by the formulae

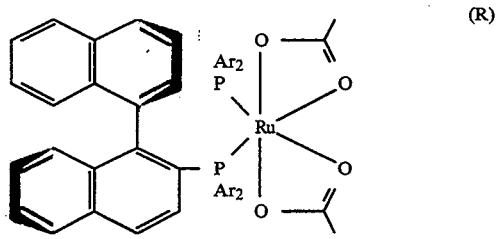

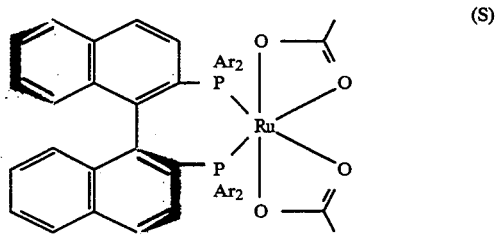

- a, Ar = C$_6$H$_5$
- b, Ar = p-CH$_3$C$_6$H$_4$
- c, Ar = p-CH$_3$OC$_6$H$_4$

OBJECT OF THE INVENTION

There is a need for a novel technical solution for the catalytic hydrogenation of ethylenically unsaturated organic compounds which is different from the technical solutions recommended by the documents EP-A-0 366 390 and EP-A-0 272 787 and the article by T. OHTA et al. cited above.

The novel technical solution which has been researched is based on the use of neutral ruthenium complexes which are structurally analogous to the compound C5 according to the article by M. COOKE et al.

SUBJECT OF THE INVENTION

According to a first feature of the invention, a novel technical solution is recommended for the catalytic hydrogenation of ethylenically unsaturated organic compounds containing at least one aliphatic C=C double bond. In fact, it has so far never been contemplated to use a compound carrying allylic ligands as a catalyst. The references indicated above, and many others, refer to various complexes of Ru with phosphines which are used for the hydrogenation of C=C bonds in a homogeneous medium, but none of the catalysts contains an allylic ligand.

In contrast to this state of affairs, the present invention results from the surprising finding that phosphine complexes of Ru in which Ru carries two allylic ligands can catalyze the asymmetric hydrogenation of C═C bonds very effectively.

Thus the present invention comprises a process for the hydrogenation of ethylenically unsaturated organic compounds in a homogeneous medium with a (diphosphino)ruthenium complex as a catalyst, wherein, in this catalyst, a ruthenium atom carries two ligands formed by allylic groups.

According to a second feature of the invention, the compounds of formula (1) below, in which Q is other than $CH_2CH_2$ when $R^1=R^2=R^3=R^4=$ methyl, are recommended as novel industrial products useful in the field of the catalytic hydrogenation of olefins and of ethylenically unsaturated organic compounds in general.

DETAILED DESCRIPTION OF THE INVENTION

The catalyst used according to the invention for the catalytic hydrogenation of ethylenically unsaturated compounds, and belonging to the group consisting of diallylic compounds of (diphosphino)ruthenium, can be represented by the schematic formula

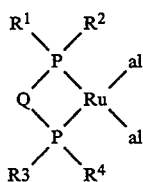
(1)

in which
al is an allylic group,
Q is a hydrocarbon bridge containing at least two catenary carbon atoms and capable of containing one to four catenary heteroatoms selected from O, S, N and Si, and
R to $R^4$ can be identical or different and are each a $C_1$—$C_{18}$-alkyl, $C_5$—$C_7$-cycloalkyl or $C_6$—$C_4$-aryl group.

The above-mentioned allylic groups al here include all allyl groups, the simplest and most economic being more precisely the allyl group itself of the formula $CH_2CH=CH_2$ and the methallyl group of the formula $CH_2C(CH_3)=CH_2$. Thus the allylic group al will advantageously be selected from the group consisting of allyl and methallyl groups. When they are bonded to the ruthenium atom, said allyl and methallyl groups have the following $al_2Ru$ configurations:

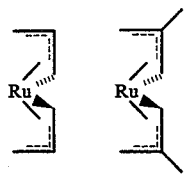

in which the allylic C═C double bond is delocalized.

The bridge Q is a chain comprising from 2 to 10 catenary atoms, it being possible for one or more fragments of this chain to be included in at least one ring. When a catenary nitrogen atom is present in said bridge Q, this nitrogen atom will be ternary, for example: —N($CH_3$)—, —N(i—$C_3H_7$)—, —N(t—$C_4H_9$)—, —N($C_6H_5$)— or —N($CH_2C_6H_5$)—. When a catenary silicon atom is present in said bridge Q, this silicon atom will be quaternary, for example: —Si($CH_3$)$_2$—, —Si($CH_2CH_3$)$_2$—, —Si($C_6H_5$)$_2$— or —Si($CH_2C_6H_5$)—.

Preferably, the bridge Q will contain from 2 to 4 catenary atoms and will advantageously have one of the following structures:

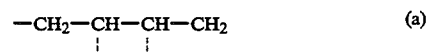 (a)

 (b)

(c)
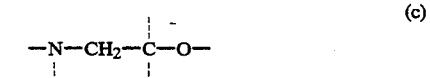

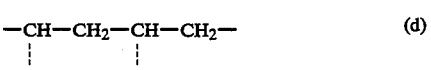 (d)

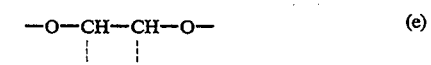 (e)

(f)

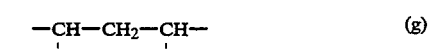 (g)

 (h)

 (i)

(j)
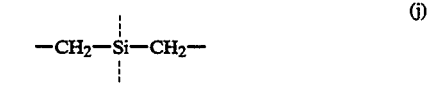

(k)

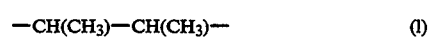 (l)

in which the dotted lines each denote a substituent other than H or else a C═C double bond on two vicinal carbon atoms included in an aryl ring; thus, when the structure $R^1R^2P$—Q—$PR^3R^4$ is the group (+)-BINAP or (−)-BINAP, the above structure (k) of the bridge Q can be

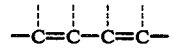

As indicated above, the groups $R^1$, $R^2$, $R^3$ and $R^4$, which are identical or different, are each a $C_1$-$C_8$-alkyl group (especially methyl, ethyl, isopropyl, propyl, butyl, s-butyl, i-butyl, t-butyl, 2,2-dimethylpropyl or 1,1,3,3-tetramethylbutyl), a $C_5$-$C_7$-cycloalkyl group (especially cyclopentyl or, preferably, cyclohexyl) or a $C_6$-$C_{12}$-aryl group (especially phenyl, tolyl, xylyl, p-methoxyphenyl, p-ethoxyphenyl, p-(t-butoxy)phenyl or naphthyl).

Preferably, $R^1$, $R^2$, $R^3$ and $R^4$, which are identical or different, will each be a cyclohexyl group, a phenyl group, a phenyl group substituted in the para-position by a $C_1$-$C_4$-alkyl group, a phenyl group substituted in the para-position by a $C_1$-$C_4$-alkoxy group, or a 2-naphthyl group.

Formula (1) as defined above encompasses the compound C5 described by M. COOKE et al. ($Q=CH_2CH_2$; $R^1=R^2=R^3=R^4=CH_3$).

With the exception of said compound C5, all the other catalysts of formula (1) are novel.

Apart from the chirality due to the bidentate groups, it is possible to introduce chirality by appropriate choice of the part P—Q—P of the molecule; in particular, it can be present on the phosphorus, in which case formula (1) has the configuration

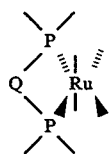

(2)

The preparation of the complexes of al$_2$Ru is known per se: it is described in the article by M. COOKE et al. cited above and in French patent application no. 89 11 159 of 23rd Aug. 1989 (published as FR-A-2 651 152 of 1st Mar. 1991).

Here attention is drawn only to the fact that a practical procedure comprises reacting an Ru salt, for example $RuCl_3.3H_2O$, with a cycladiene, in particular cyclooctadiene. The resulting complex is reacted with an organomagnesium compound of the formula XMg-al (in which al is the allyl or methallyl group, as indicated above, and X is F, Cl, Br or I) to form a complex cyclooctadiene-Ru(al$_2$). The latter is then heated, in general at about 50° to 70° C. for several hours in an appropriate solvent, with a diphosphine

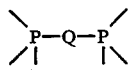

to form the complex (1) or (2).

This process will advantageously be carried out with an organomagnesium compound XMg-al in which X will be Cl and al will be the methallyl group [i.e. $CH_2=C-(CH_3)CH_2MgCl$].

The diphosphines which can be used are the various compounds known in the art by abbreviations such as "DIOP", "CHIRAPHOS", "NORPHOS", "BNPE", "BINAP", "DIPAMP", "BDPP" etc., which replace the cycloalkadiene to form the asymmetric catalyst.

As such names are used in the Examples which follow, their compositions are specified below by means of formulae:

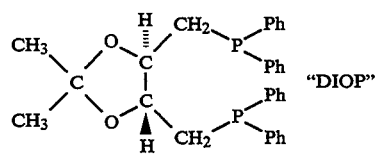

-continued

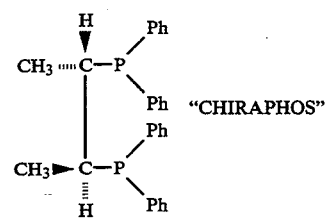

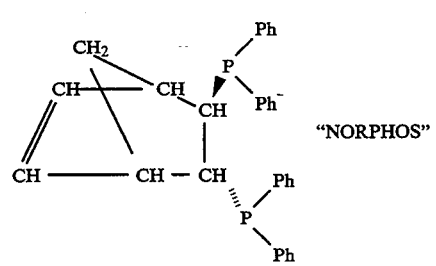

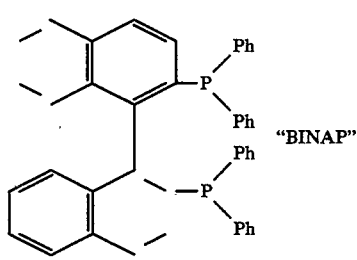

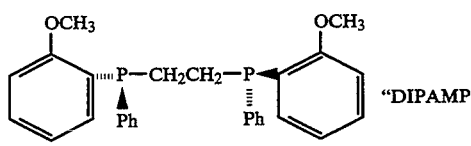

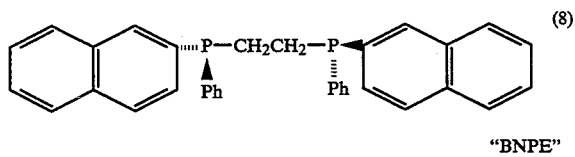

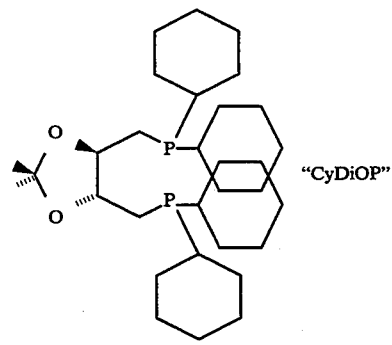

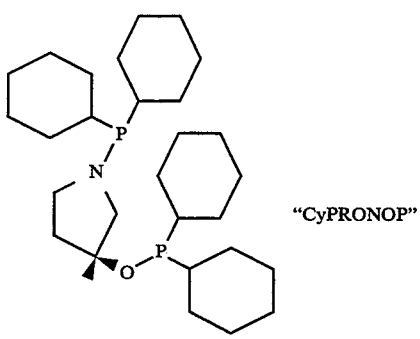

"CyPRONOP" (10)

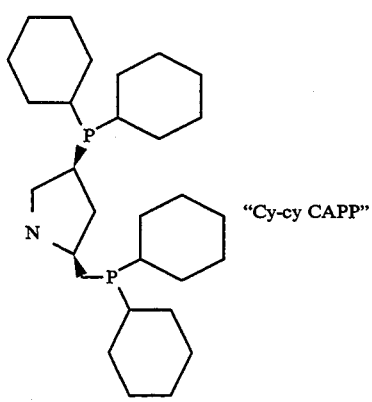

"Cy-cy CAPP" (11)

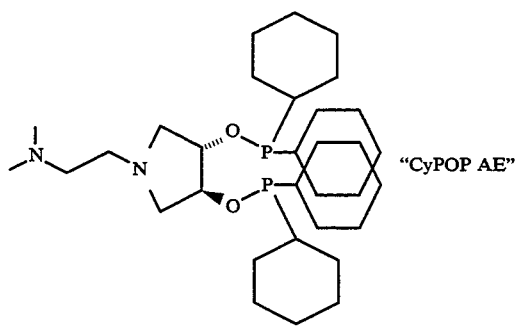

"CyPOP AE" (12)

These phosphines listed above are mentioned here without implying a limitation.

By virtue of the mild phosphination conditions, indicated above, which are applied in the preparation of the novel catalysts, various tertiary mono- or di-phosphines carrying chirality on the P atom can be obtained without the ligands of the complex undergoing racemization, which becomes substantial above 80° C.

In contrast to the technique of the prior art, which practically only used the rather expensive diphosphine "BINAP" to successfully hydrogenate C=C double bonds (MASATO KITAMURA, J. Org. Chem., 1987, 52, pages 3176–3178), the present invention makes it possible to change ligands easily: this particularly concerns ligands carrying chirality on the phosphorus. As shown in the Examples, the invention permits the economic asymmetric hydrogenation of olefinic bonds with Ru catalysts having different ligands.

The invention is illustrated by the following non-limiting Examples, of the hydrogenation of the olefinic double bond,

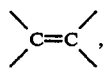

in carboxylic acids. Thus, according to the invention, an olefin can be reduced when it carries one or more functional groups.

According to the present invention, the hydrogenation is generally carried out in a solution containing 0.1 to 3 mol of unsaturated compound to be treated per liter of an appropriate solvent, which, depending on the particular case, can be for example an anhydrous alcohol, especially methanol, ethanol, propanol, etc., or a hydrocarbon such as benzene, toluene, xylene, pentane, hexane, heptane or the like, or optionally a mixture of such solvents. An amount of 0.1 to 5 mol % of catalyst, based on the unsaturated compound, is dissolved in the solvent. Proportions of about 0.5 to 2 mol % of catalyst are generally suitable.

In the Examples which follow, the hydrogenation procedure was carried out as indicated below. 1 mmol of olefinic substrate to be hydrogenated and 3 ml of degassed dry methanol are introduced into a reactor containing an argon atmosphere. 1 mol % of catalyst, consisting of a phosphine complex of Ru, is added. The argon atmosphere is then replaced with hydrogen and a hydrogen pressure with a value of 1 to 100 bar is established. The mixture is stirred for 24 to 64 hours at 20° C. Experience has moreover shown that the preferred temperatures for such hydrogenations range from 0° to 50° C.

After evaporation of the solvent, the degree of conversion of the olefinic product to the corresponding saturated compound is determined by NMR.

The Examples whose results are given below correspond to the use of the catalysts according to the invention, containing two methallyl groups bonded to the Ru atom.

EXAMPLES 1 to 7

2-Methylbut-2-enoic acid:

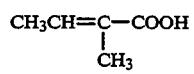

is hydrogenated by the procedure stated above to give 2-methylbutanoic acid:

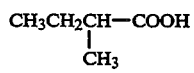

at 20° C., under different pressures and for variable times.

The catalyst DIOP-Ru(methallyl)$_2$ had the following characteristics:

$^1$H NMR (250 MHz, C$_6$D$_6$): 1.0 (m, 2H); 1.3 (s, 6H); 1.32 (q, J=14.5 Hz, 4H); 2.04 (s, 6H); 2.55 (m, 2H); 2.79 (dd, J$_1$=8.5 Hz, J$_2$=13 Hz, 6H); 3.25 (t, J=13 Hz, 6H); 4.15 (m, 2H); 6.8–8.0 (m, 20H, aromatic). $^{13}$C NMR (62 MHz, C$_6$D$_6$): 25.77; 27.2; 31.5 (m); 42.5; 48.31 (m); 78.8; 95.7; 107.9; 127–140 (aromatic). $^{31}$P NMR (100 MHz, C$_6$D$_6$): 36 (ref. 75% H$_3$PO$_4$). IR (Nujol): 1595, 1240 cm$^{-1}$. $\alpha_D^{25} = +202°$ (c=0.43, toluene). Melting point: 204° C. (decomposition).

The characteristics of the catalyst CHIRAPHOS-Ru(methallyl)$_2$ were as follows:

$^1$H NMR (250 MHz, C$_6$D$_6$): 1.06 (d, J=6.5 Hz, 2H); 1.12 (d, J=6.5 Hz, 2H); 1.24 (q, J=2.5 Hz, 6H); 1.61 (d, J=2.5 Hz, 2H); 1.74 (d, J=2.5 Hz, 2H); 2.15 (J, 6H); 6.8–8.0 (m, 20H, aromatic). IR (Nujol): 1580, 1085, 1015, 760, 720 cm$^{-1}$. $\alpha_D^{25} = +60°$ (c=0.2, toluene). Melting point: 183° C. (decomposition). (See Table 1 below.)

EXAMPLE 8

Hydrogenation of 2-methylhex-2-enoic acid of the formula

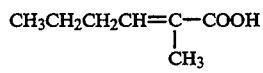

to 2-methylhexanoic acid of the formula

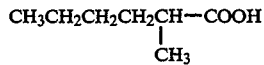

at 20° C., under a hydrogen pressure of 15 bar, for 24 hours.

The catalyst CHIRAPHOS-Ru(methallyl)$_2$ gives an enantiomeric excess (ee) of 17% with a yield of 100%.

EXAMPLE 9

Hydrogenation of 3-phenyl-2-methylprop-2-enoic acid of the formula

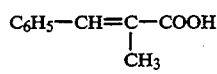

to 3-phenyl-2-methylpropanoic acid of the formula

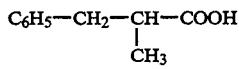

The reaction is carried out at 20° C. under a hydrogen pressure of 95 bar for 24 hours. The catalyst CHIRAPHOS-Ru(—)(methallyl)$_2$ gives the saturated acid with a yield of 70%.

EXAMPLE 10

Hydrogenation of 2-(6-methoxy-2-naphthyl)prop-2-enoic acid to 2-(6-methoxy-2-naphthyl)propionic acid, which is known in pharmacy as "NAPROXENE" and possesses antiinflammatory properties.

The operation takes place at room temperature, under a hydrogen pressure of 30 bar, for 64 hours, in the presence of the complex DIPAMP-Ru(methallyl)$_2$ as the catalyst and 10% of triethylamine.

The reaction

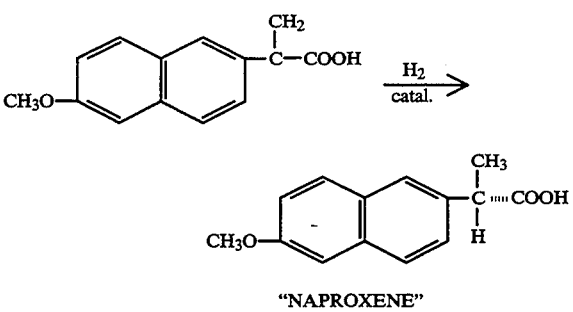

"NAPROXENE"

gives a yield of 100% and the product has an ee of 55%.

The characteristics of the catalyst DIPAMP-Ru-(methallyl)$_2$ employed are as follows:

$^1$H NMR (250 MHz): 0.25 (d, J=15, 2H); 1.1 (dd, J$_1$=15, J$_2$=5, 2H); 1.7 (s, 2H); 2.2 (d, J=2 Hz, 2H); 2.31 (s, 6H); 2.92 (s, 6H); 3.4 (m, 2H); 6.5–8.1 (m, 18H).

$^{13}$C NMR (CDCl$_3$): 26.6; 32.5 (dd, J$_1$=J$_2$=27 Hz); 42.4 (d, J=25 Hz); 44.3; 54.6; 96.1; 110.6; 120.6; 126–130; 134.6; 142.3; 159.9. Color: yellow. M.p.=183°–185° (decomposition). $\alpha_D$=$-43.5°$ (c=0.23, toluene).

EXAMPLE 11

A hydrogenation similar in all respects to that of Example 10 is carried out with the complex DIPAMP-Ru(AcO)$_2$ as the catalyst. The yield is again 100% but the ee is only 22%, which shows the advantage of the allylic groups in the catalyst of Example 10.

It may be advantageous in some cases to use an Ru complex having allylic ligands together with a corresponding complex without allylic groups; the preferred relative proportions are then 10 to 90 parts by weight of the one to 90 to 10 parts of the other.

TABLE I

Hydrogenation of CH$_3$—CH=C(CH$_3$)—COOH at 20° C.

| Ex. no. | CATALYST | Pressure (bar) | Time (h) | Yield % | ee % | Configuration |
|---|---|---|---|---|---|---|
| 1 | DIOP—Ru(—)(methallyl)$_2$ | 50 | 24 | 100 | 46 | R |
| 2 | " | 15 | " | 100 | 46 | R |
| 3 | " | 5 | " | 100 | 48 | R |
| 4 | " | 1.5 | 36 | 100 | 51 | R |
| 5 | CHIRAPHOS—Ru(—)(methallyl)$_2$ | 15 | 24 | 100 | 30 | S |
| 6 | NORPHOS—Ru(+)(methallyl)$_2$ | 1.5 | 60 | 100 | 4 | S |
| 7 | BINAP—Ru(+)(methallyl)$_2$ | 15 | 24 | 100 | 87 | R |

EXAMPLE 12

Hydrogenation of α-acetamido-2-phenylprop-2-enoic acid of the formula

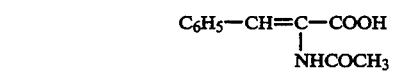

to N-acetylphenylalanine of the formula

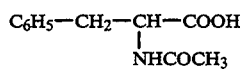

The reaction is carried out at 20° C. under a hydrogen pressure of 100 bar for 24 hours, the catalyst being DIPAMP-Ru(methallyl)$_2$. The N-acetylphenylalanine is obtained with a yield of 70%.

EXAMPLES 13 to 21.

9 chiral ruthenium complexes of formula (1) according to the invention were prepared from ruthenium chloride trihydrate and cyclooctadiene in accordance with the following reaction mechanisms, where met is the methallyl group.

(I)

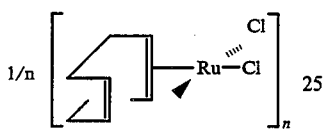

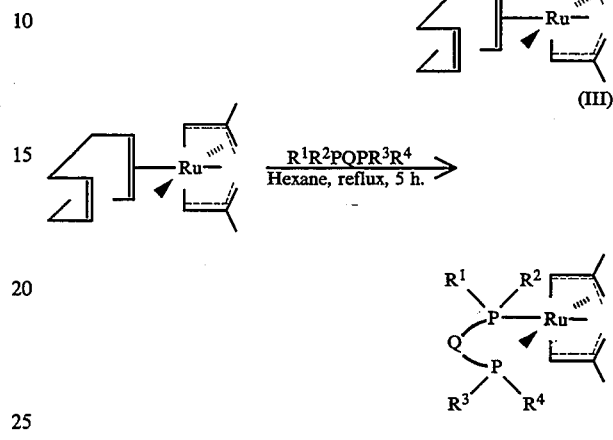

The chiral compounds obtained from different diphosphines according to equation III are shown in Table II below.

TABLE II

| | LIGAND | | COMPLEX |
|---|---|---|---|
| Ex. 13 | (structure) | (−)BDPP (2S, 4S)-2,4-bis(diphenylphosphino)pentane (S,S) M = 440.50 | (−)PDPPRu(met)$_2$ M = 649.76 (Green) Yield = 60% |
| Ex. 14 | (structure) | (+)DIOP (S, S)—O,O-isopropylidene-2,3-dihydroxy-1,4-bis(diphenylphosphino)-butane M = 498.54 | (+)DIOPRu(met)$_2$ M = 707.80 (Yellow) Yield = 90% |

TABLE II-continued

| | LIGAND | COMPLEX |
|---|---|---|
| Ex. 15 | 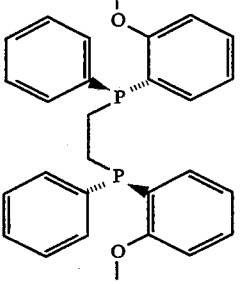 (−)DIPAMP (R, R)-1,2-bis-(phenylorthoanisyl-phosphino)ethane M = 458.48 | (−)DIPAMP-Ru(met)$_2$ M = 667.74 (Yellow) Yield = 40% |
| Ex. 16 | 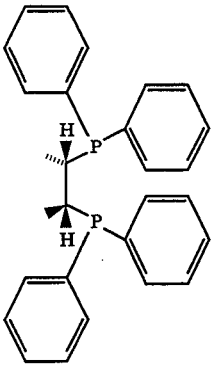 (−)CHIRAPHOS (S, S)-2,3-bis-(diphenylphos-phino)butane M = 426.48 | (−)CHIRAPHOS-Ru(met)$_2$ M = 635.74 (Yellow) Yield = 55% |
| Ex. 17 | 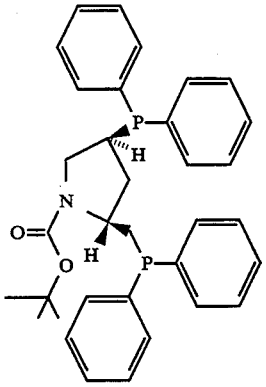 (−)BPPM (2S, 4S)—N—BOC-4-diphenylphosphino-2-diphenylphos-phino-2-methyl-pyrrolidine M = 553.63 | (−)BPPMRu(met)$_2$ M = 762.88 (Pale green) Yield = 67% |
| Ex. 18 | 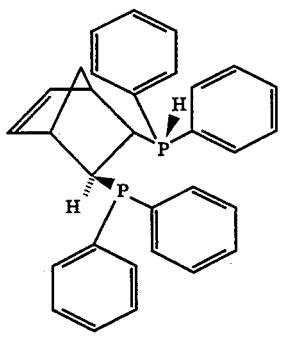 (+)NORPHOS (S, S)-1,2-bis(di-phenylphosphino)-bicyclo[2.2.1]hept-4-ene M = 462.61 | (+)NORPHOS-Ru(met)$_2$ M = 671.77 (Brown) Yield = 71% |

TABLE II-continued

| | LIGAND | COMPLEX |
|---|---|---|
| Ex. 19 | (+)BINAP<br>(R)-2,2'-bis(di-<br>phenylphosphino)-<br>1,1'-binaphthyl<br>M = 622.69 | (+)BINAP-<br>Ru(met)$_2$<br>M = 831.95<br>(Brown)<br>Yield = 32% |
| Ex. 20 | (−)BNPE<br>Bis(naphthyl-<br>phenylphosphino)-<br>ethane<br>M = 498.54 | (−)BNPERu(met)$_2$<br>M = 606.73<br>(Bright yellow)<br>Yield 45% |
| Ex. 21 | "BNPPMDS"<br>Bis(naphthylphenyl-<br>phosphinomethano)-<br>diphenylsilane<br>M = 684.88 | "BNPPMDS"-<br>Ru(met)$_2$<br>M = 898.17<br>(Brown)<br>Yield = 74% |

These complexes are kept in a refrigerator under an argon atmosphere.

EXAMPLES 22 to 29

8 of the chiral ruthenium complexes shown in Table II above (those of Examples 13 to 20) were studied as catalysts in the preparation of tiglic acid by catalytic hydrogenation.

This was done by carrying out the reaction of equation IV below using 1% of each chiral complex in methanol, with hydrogen under a pressure of 8.1 bar (8 atmospheres), at 25° C., for 24 h.

The results obtained have been collated in Table III below, where met denotes the methallyl group.

TABLE III (IV)

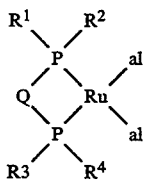

| Experiment | Catalyst | Yield %[1] |
|---|---|---|
| 22 | BDPPRu(met)$_2$ | 100 |
| 23 | DIOPRu(met)$_2$ | 100 |
| 24 | DIPAMPRu(met)$_2$ | 100 |
| 25 | CHIRAPHOSRu(met)$_2$ | 100 |
| 26 | BPPMRu(met)$_2$ | 100 |
| 27 | NORPHOSRu(met)$_2$ | 100 |
| 28 | BINAPRu(met)$_2$ | 100 |
| 29 | BNPERu(met)$_2$ | 100 |

[1]Determined by $^1$H NMR.

For practical reasons, it is preferable according to the invention to use chiral ruthenium complexes of formula (1) in which the group $R^1R^2P$—Q—$PR^3R^4$ contains a total of more than 6 carbon atoms, preferably more than 12 carbon atoms and particularly preferably from 24 to 50 carbon atoms.

What is claimed is:

1. A process for the catalytic hydrogenation of ethylenically unsaturated organic compounds employing a catalyst which is a ruthenium-phosphorous complex of the formula $$\begin{array}{c} R^1 \quad R^2 \\ \diagdown \diagup \\ P \\ \diagup \quad \diagdown al \\ Q \quad Ru \\ \diagdown \quad \diagup al \\ P \\ \diagup \diagdown \\ R^3 \quad R^4 \end{array}$$

in which
al is allyl or methallyl group,
Q is a bridge containing 2-10 catenary atoms in its linear chain linking the two phosphorous atoms and having at least two catenary carbon atoms, wherein Q is such that the group $R^1R^2PQPR^3R^4$ contains more than 6 up to 50 carbon atoms and $R^1$ to $R^4$ are individually a $C_1$-$C_{18}$-alkyl, $C_5$-$C_7$-cycloalkyl or $C_6$-$C_{12}$-aryl group, and the group $R^1R^2P$—Q—$PR^3R^4$ contains a total of more than 6 carbon atoms up to 50 carbon atoms.

2. A process according to claim 1 wherein al is methallyl.

3. A process according to claim 1 wherein, in the catalyst used, the ruthenium is complexed with a chiral diphosphine, on each P atom.

4. A process according to claim 1 wherein the ethylenically unsaturated compound which is hydrogenated is in solution in a concentration of from 0.1 to 3 mol per liter of solvent, and the solvent contains the catalyst in a proportion of 0.1 to 5 mol % based on the unsaturated compound.

5. A process according to claim 1 wherein the hydrogenation is carried out under an $H_2$ pressure of 1 to 100 bar and at a temperature of 0° to 50° C.

6. A process according to claim 4 wherein the reaction medium also contains a non-allylated catalyst.

7. A process according to claim 1 wherein said bridge Q is a fragment of at least one ring.

8. A process according to claim 1 wherein the group $R^1R^2P$—Q—$PR^3R^4$ contains more than 12 carbon atoms.

9. A process according to claim 1 wherein $R^1$, $R^2$, $R^3$ and $R^4$, which are identical or different, are each a cyclohexyl group, a phenyl group, a phenyl group substituted in the para-position by a $C_1$-$C_4$-alkyl group, a phenyl group substituted in the para-position by a $C_1$-$C_4$-alkoxy group, or a 2-naphthyl group.

10. A chiral ruthenium complex useful as a catlyst in the catalytic hydrogenation of ethylenically unsaturated organic compounds, said chiral complex having the formula

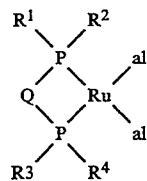

in which
al is an allyl or methallyl group,
Q is a bridge containing 2-10 catenary atoms in its linear chain linking the two phosphorous atoms and having at least two catenary carbon atoms and
$R^1$ to $R^4$ are individually a $C_1$-$C_{18}$-alkyl, $C_5$-$C_7$-cycloalkyl or $C_6$-$C_{12}$-aryl group, and the group $R^1R^2P$—Q—$PR^3R^4$ contains a total of more than 6 carbon atoms and up to 50 carbon atoms.

11. A complex according to claim 10 wherein the group $R^1R^2P$—Q—$PR^3R^4$ in its molecule consists of one of the diphosphines known by the abbreviations "DIOP", "CHIRAPHOS", "NORPHOS", "BINAP", "DIPAMP", "BNPE", "CyDIOP", "CyPRONOP", "Cy-CyCAPP", "CyPOP AE", "BDPP", "BPPM" and "BNPPDS".

12. A process according to claim 4, wherein the solvent contains the catalyst in a proportion of 0.5 to 2 mol percent based on the unsaturated compound.

13. A process according to claim 5, wherein the hydrogenation is carried out for 24-64 hours.

14. A process according to claim 8, in which said $R^1R^2P$—Q—$PR^3R^4$ group contains 24-50 carbon atoms.

15. A complex according to claim 10, in which said $R^1R^2P$—Q—$PR^3R^4$ group contains more than 12 carbon atoms.

16. A complex according to claim 10, in which said $R^1R^2P$—Q—$PR^3R^4$ group contains 24-50 carbon atoms.

17. A complex according to claim 10, in which said $R^1$, $R^2$, $R^3$ and $R^4$ are individually selected from the group consisting of cyclohexyl, unsubstituted phenyl and phenyl substituted in the para-position by a 1 to 4 carbon atom alkoxy group or a 2-naphthyl group.

* * * * *